US 6,677,399 B2

(12) United States Patent
Herbert et al.

(10) Patent No.: US 6,677,399 B2
(45) Date of Patent: Jan. 13, 2004

(54) AGROCHEMICAL FORMULATIONS

(75) Inventors: Richard Michael Herbert, Oxford, PA (US); Jonathan Mercer Watkins, Daventry (GB); Martin Charles Crossman, Hixson, TN (US); Youry Den Tandt, Sint-Amands (BE); Steven Irene Jozef Reekmans, Brussels (BE); Frank Dirk Jozef Hartmann, Wilmington, DE (US)

(73) Assignee: Imperial Chemical Industries PLC, London (GB)

(*) Notice: Subject to any disclaimer, the term of this patent is extended or adjusted under 35 U.S.C. 154(b) by 0 days.

(21) Appl. No.: 09/975,071

(22) Filed: Oct. 12, 2001

(65) Prior Publication Data

US 2002/0099131 A1 Jul. 25, 2002

Related U.S. Application Data

(63) Continuation of application No. PCT/GB00/01381, filed on Apr. 11, 2000.
(60) Provisional application No. 60/129,900, filed on Apr. 16, 1999.

(30) Foreign Application Priority Data

Apr. 12, 1999 (GB) .............................................. 9908249

(51) Int. Cl.$^7$ ................................................ C08L 41/00
(52) U.S. Cl. ...................................................... 524/547
(58) Field of Search ......................................... 524/547

(56) References Cited

U.S. PATENT DOCUMENTS

| 4,252,556 A | * | 2/1981 | Nadasy et al. | ............... 504/224 |
| 5,435,821 A | * | 7/1995 | Duvdevani et al. | ............. 71/28 |
| 6,458,745 B1 | * | 10/2002 | Runge et al. | ................ 504/359 |

FOREIGN PATENT DOCUMENTS

| DE | 3707616 | | 9/1987 |
| EP | 0697422 | | 2/1996 |
| JP | 62036302 | | 2/1987 |
| JP | 5017303 | | 1/1993 |
| WO | WO 98/16105 | * | 4/1998 |
| WO | 9918785 | | 4/1999 |

* cited by examiner

Primary Examiner—Bernard Lipman
(74) Attorney, Agent, or Firm—Pillsbury Winthrop LLP

(57) ABSTRACT

Water dispersible solid granular agrochemical formulations, typically in the form of wettable powders, particularly having an average particle size from 5 to 50 μm, or water dispersible granules, particularly having an average particle size of from 200 μm to 5 mm, include one or more water dispersible agrochemical active components; and a dispersing agent including a water dispersible styrene (meth) acrylic copolymer. The copolymeric dispersing agent may include monomer residues which include strongly acidic, particularly sulphonic acid groups.

56 Claims, No Drawings

AGROCHEMICAL FORMULATIONS

CROSS REFERENCE TO RELATED APPLICATIONS

This application is a continuation from International Application PCT/GB00/01381 filed Apr. 11, 2000 which designated the U.S. and was published under PCT Article 21(2) in English, and further claims priority from U.S. Provisional Application No. 60/129,900 filed Apr. 16, 1999, which are both incorporated herein by reference.

This invention relates to agrochemical formulations and in particular to such formulations in solid granular form and especially to such formulations where the granules are dispersible in water.

Agrochemical formulations are commonly applied by spraying, usually in an aqueous medium, in which the active agrochemical may be dissolved, dispersed or emulsified either as such or dissolved in a water immiscible solvent. In meeting the demand for a reduction in the risk to the end user, solid formulations are attractive because the active agrochemical is immobilised, and solid formulations can be of higher density than liquid formulations. It is also desirable that the water dispersible granule form of the agrochemical formulation is non-dusting and typically has a particle size of from 200 $\mu$m to 2 mm. The dusting tendency of the granules can be improved (dusting reduced) by using binder materials in making the solid formulation, but this may detract from the speed and extent to which the granules disintegrate when placed in water especially if the binder is not water soluble. Materials in current use for this function include, polyvinylpyrrolidone (PVP), polyvinyl alcohol (PVOH), carbomethoxycellulose (CMC), starch, alginate, gum arabic, sorbitol, and sucrose.

Dispersing agents are commonly included in agrochemical water dispersible granules to help disperse the active ingredient in water. Examples of conventional dispersing agents include sodium and ammonium salts of naphthalene sulfonate formaldehyde condensates; sodium, calcium and ammonium salts of lignosulfonates; sodium and ammonium salts of maleic anhydride copolymers and sodium salts of condensed phenolsulphonic acid.

The present invention is generally directed to agrochemicals in the form of water dispersible granules including styrene (meth)acrylic copolymers as dispersing agents for the agrochemical on mixing with water and in particular can provide good dispersion and suspension properties after extended storage (ageing) of the dry granules.

The present invention accordingly provides an agrochemical formulations in solid granular form which is dispersible in water and which includes:

1 one or more water dispersible agrochemical active components; and 2 a dispersing agent including a water dispersible styrene (meth)acrylic copolymer.

The present invention includes an agrochemical formulation in solid granular form which is dispersible in water and which includes:

1 one or more water dispersible agrochemical active components;

2 a dispersing agent including a water dispersible styrene (meth)acrytic copolymer; and at least one of:

3 one or more solid support materials;

4 one or more wetting agents;

5 one or more adjuvants; and/or 6 one or more water soluble matrix materials.

In particular, the invention provides an agrochemical formulations in solid granular form which is dispersible in water and which includes:

1 one or more water dispersible agrochemical active components;

2 a dispersing agent including a water dispersible styrene (meth)acrylic copolymer;

3 one or more solid support materials; and 4 one or more wetting agents; and optionally 5 one or more adjuvants; and/or 6 one or more water soluble matrix materials.

The invention includes a method of making a spray mix in which an agrochemical formulation in solid granular form of the invention is dispersed in water. The invention further includes a method of treating plants in which the plants or the soil surrounding the plants are sprayed with a spray mix made by dispersing an agrochemical formulations in solid granular form of the invention in water.

The water dispersible styrene (meth)acrylic copolymer used in this invention is for convenience sometimes referred to below as a polymeric dispersant. The polymeric dispersant is a styrene (meth)acrytic acid copolymer. The repeating units in the copolymer are conveniently considered as residues of monomer components.

The (meth)acrylic acid monomer(s) can be acrylic acid, methacrylic acid, crotonic acid or a mixture of two or more of these. The (meth)acrylic acid monomer(s) can be or include (meth)acrylic monomers which are derivatives of (meth)acrylic acid which include strong acid, especially sulphate acid or sulphonic acid groups (or their salts). Examples of such monomers include acrylamido methyl propyl sulphonate (AMPS) and (meth)acrylic acid isethionate. When present such strong acid modified monomers usually form from 1 to 30 mole %, more usually 2 to 20 mole %, and desirably from 5 to 15 mole %, of the acrylic acid monomers in the copolymer.

The styrene monomer(s) can be, and desirably is, styrene as such or a substituted styrene particularly a hydrocarbyl, desirably alkyl, substituted styrene, in which the substituent (s) are on the vinyl group or on the aromatic ring of the styrene e.g. α-methyl styrene and vinyl toluene. As with the (meth)acrylic acid monomer, the styrene monomer can be or include styrene monomers including strongly acid, particularly sulphonic acid substituents. When present such strong acid modified monomers usually form from 1 to 30 mole %, more usually 2 to 20 mole %, and desirably from 5 to 15 mole %, of the styrene monomers in the copolymer.

In the water dispersible styrene (meth)acrylic copolymer used in the invention, the molar ratio of residues of the (meth)acrylic acid monomer(s) to those of the styrene monomer(s) is generally from 20:1 to 1:5, more usually 10:1 to 1:2 and particularly from 3:1 to 1:1. Generally correspondingly, the proportions of residues of the monomers by weight are typically from 93 to 10%, more usually 87 to 25%, particularly 67 to 40%, of the (meth)acrylic acid monomer(s) and from 7 to 90%, more usually 13 to 75%, particularly 33 to 60%, of the styrene monomer(s).

Other monomers, such as acidic monomers e.g. itaconic acid or maleic acid or anhydride; strongly acidic monomers such as methallyl sulphonic acid (or a salt); or non-acidic acrylic monomers e.g. acrylic esters which may be alkyl esters particularly $C_1$ to $C_6$ alkyl esters such as methyl methacrylate, butyl methacrylate or butyl acrylate or hydroxy alkyl esters particularly $C_1$ to $C_6$ hydroxyalkyl esters such as hydroxy ethyl methacrylate, or hydroxy propyl methacrylate; or vinyl monomers such as vinyl acetate, can be included. Typically, the proportion of such other monomer(s) will be not more than about 25 mole %, usually not more than about 15 mole %, more usually not more than about 5 mole %, of the total monomers used. The proportion by weight of other monomers will typically be not more than about 30%, usually not more than about 20%, more usually not more than about 10%.

The polymeric dispersant can be a single styrene acrylic acid copolymer or a blend including two or more such copolymers. In particular, when strong acid residues are included in the polymeric dispersant, the dispersant can be a blend of copolymer including strong acid residues and copolymer not including such residues. In such blends, it is generally desirable that the ratio of such copolymers is from 1:10 to 10:1, more usually 5:1 to 1:5, by weight. In particular, the proportion of copolymer including strong acid residues is desirably at least 25%, more usually at least 40%, by weight of the polymeric dispersant.

When strong acid residues are included in the polymeric dispersant, the overall proportion of monomer residues including strong acid groups is desirably from 0.25 to 25 mole %, more usually from 0.5 to 20 mole % and desirably from 1 to 10 mole %.

The inclusion of monomers having strongly acidic substituent groups in the polymeric dispersant can provide improved dispersion of the solid granular form of the agrochemical formulations when dispersed in hard water, particularly water having a hardness above 500 ppm e.g. up to 1000 ppm, up to 2000 ppm or even up to 5000 ppm.

The polymeric dispersant desirably has a molecular weight of from 750 to 20000, more desirably from 1000 to 10000 and particularly from 1500 to 5000. The polymeric dispersant can be used as the free acid or as a salt. In practice, the form present in a formulation will be determined by the acidity of the formulation. Desirably, the formulation will be near neutral and so most of the acid groups will be present as salts. The cations in any such salt can be alkali metal, particularly sodium and/or potassium, ammonium, or amine, including alkanolamine such as ethanolamine, particularly tri-ethanolamine. Polymeric dispersants used in this invention are desirably free from solvent which might interfere with the active ingredient or cause the granules to stick together. Also it is useful if the polymeric dispersant can be used satisfactorily in a variety of different granulation processes. Further desirably the polymeric dispersant is heat stable, readily soluble in cold water from the solid dispersible granule (satisfactory polymeric dispersants need not be readily cold water soluble from the bulk solid form) and non gelling.

The polymeric dispersants can be made by free radical initiated polymerisation, e.g. using a peroxide or a redox initiator, particularly by solution polymerisation, of the constituent monomers, optionally also with a chain transfer agent such as an alkyl mercaptan which acts to control the molecular weight of the polymer. Suitable methods are described for example in EP 0697422 A.

To aid dispersion of the active component(s) in the spray formulation after dilution with water, it is desirable that the polymeric dispersant is compatible with and more usually interacts strongly with, the surface of any water insoluble active agrochemical present in the formulation. Water insoluble agrochemical actives may be used as powders, absorbed/adsorbed onto solid support material or, particularly for liquid actives, in microencapsulated form. Desirably when microencapsulated actives are used the polymeric dispersant is also desirably compatible with common shell wall materials used in such microcapsules e.g. polyurea, polyurethane, polyester, polycarbonate, polysulfonamide and polyamide.

The dispersing agent used in the formulation of the invention may be wholly of styrene (meth)acrylic copolymers or it may include other dispersant materials such as the conventional dispersants mentioned above, such as naphthalene sulfonate formaldehyde condensates, lignosulfonates, maleic anhydride copolymers and condensed phenolsulphonic acid and their salts. When used in such combinations the weight ratio of styrene (meth)acrylic copolymer(s) to such conventional dispersants will usually be at least 1:5 and more usually from 1:4 to 10:1, particularly from 1:2 to 5:1.

Other conventional dispersants and dispersing aids such as polyvinylpyrrolidone (PVP), polyvinyl alcohol (PVOH), phosphate esters such as the tristeryl phenol based phosphate esters available as Soprofor FL, carbomethoxycellulose (CMC), starch, alginate, gum arabic, sorbitol, and sucrose (as mentioned above) can be included. When used such conventional materials are typically used as minor components of the dispersing agent e.g. at from 1 to 20% by weight of the total dispersant.

The agrochemical active material can be one or more of a wide range of water dispersible agrochemically active materials. Description of the actives as water dispersible means that they are water soluble or can be dispersed in water, if necessary with the use of dispersing agents. Specifically, it may be one or more plant growth regulators, herbicides, and/or pesticides, for example insecticides, fungicides, acaricides, nematocides, miticides, rodenticides, bactericides, molluscicides and bird repellants. Usually, the active will be a water insoluble or immiscible material, although granules can be made including water soluble active materials. Specific examples of actives include:

Herbicides: including triazines such as Atrazine {6-chloro-N-ethyl-N'-(1-methylethyl)-1,3,5-triazine-2,4-diamine, and Prometryn {N,N'-bis(1-methylethyl)-6-(methylthio)-1,3,5-triazine)-2,4-diamine}, substituted ureas such as Diuron {N'-(3,4-dichlorophenyl)-N,N-dimethylurea}, sulphonyl ureas such as metsulfuron-methyl {2-[[[[(4-methoxy-6-methyl-1,3,5triazin-2-yl) amino] carbonyl]amino]sulfonyl]benzoate}, triasulfuron {2-(2-chloroethoxy)-N-[[(4-methoxy-6-methyl-1,3,5-triazin-2-yl) amino]carbonyl]benzenesulfonamide}, tribenuron-methyl {methyl 2-[[[[(4-methoxy-6-methyl-1,3,5triazin-2-yl) methylamino]carbonyl]amino]sulfonyl]benzoate} and chlorsulfuron {2-chloro-N-[[(4-methoxy-6-methyl-1,3, 5triazin-2-yl)amino]carbonyl]benzenesulfonamide}, bis-carbamates such as Phenmedipham {3-[(methoxycarbonyl) amino]phenyl (3-methylphenyl)carbamate};

Fungicides: including thiocarbamates, particularly alkylenebis(dithiocarbamate)s, such as Maneb {[1,2-ethanediylbis-[carbamodithiato](2-)]manganese} and Mancozeb {[[1,2-ethanediyl-bis[carbamodithiato]](2-)] manganese mixture with [[1,2-ethanediylbis [carbamodithiato]](2-)]zinc}, strobilurins such as azoxystrobin {methyl (E)-2-[[6-(2-cyanophenoxy)-4-pyrimidinyl]oxy]-a-(methoxymethylene)benzeneacetate} and kresoxim-methyl {(E)-a-(methoxyimino)-2-[(2-methylphenoxy)methyl]benzeneacetic acid methyl ester}, dicarboximides such as iprodione {3-(3,5dichlorophenyl)N-isopropyl-2,4dioxo imidazolidine-1-carboxamide}; azoles such as propiconazole {1-[2-(2,4-dichloro-phenyl)-4-propyl-1,3-dioxolan-2-yl-methyl-1H-1,2,4-triazole}, and tebuconazole {(RS)-1-p-chlorophenyl-4,4-dimethyl-3-(1H-1,2,4-triazole-1-ylmethyl)pentan-3-ol}; halophthalonitriles such as chlorothalonil {2,4,5,6-tetrachloro-1,3-dicyanobenzene}; and inorganic fungicides such as Copper hydroxide {Cu(OH)$_2$};

Insecticides: including benzoyl ureas such as Diflubenzuron {N-[[(4-chlorophenyl)amino]carbonyl]-2,6-difluorobenzamide)}; and carbamates such as carbaryl {1-naphthyl methylcarbamate};

Acaricides including: tetrazines such as Clofentezine {3,6-bis(2-chlorophenyl)-1,2,4,5-tetrazine}.

Among water soluble active materials, non-selective herbicides, particularly N-(phosphono-methyl)glycine type herbicides such as glyphosate and sulphosate {respectively the iso-propyl-amino and trimethylsulphonium salts of N-phosphonomethyl glycine} and phosphinyl amino acids such as glufosinate {2-amino-4-(hydroxymethylphosphinyl) butanoic acid}, particularly as the ammonium salt. Such water soluble actives can be used as the sole active in water dispersible granules, but more usually, they will be used in combination with water insoluble or immiscible actives in multi-active formulations.

The granules can include solid support, filler or diluent material(s) which is desirably inert to the agrochemically active material, but which is readily dispersible in water, if necessary in conjunction with dispersing agents. They may also have the benefit of reducing granule dry clumping and the disintegration rate (on addition to water) and can also be used to adjust the active ingredient concentration. Examples include clays such as kaolin (china clay) and bentonite clays, which may be natural bentonites or modified e.g. activated bentonites, synthetic and diatomaceous silicas, calcium and magnesium silicates, titanium dioxide, aluminium, calcium or magnesium carbonate, ammonium, sodium, potassium, calcium or barium sulphate, charcoal, starch, including modified starches such as alkyl and carboxyalkyl starches, cellulose, such as microcrystalline cellulose, and cellulose derivatives such as carboxyalkyl cellulose, and mixtures of two or more such solid support, filler, diluent materials.

The agrochemical formulation can include adjuvants, particularly surfactant adjuvants, especially non-ionic surfactants, such as alcohol alkoxylates e.g. ethoxylates, particularly of $C_8$ to $C_{18}$ alcohols which can be linear, branched or linear/branched mixtures; alkylamine alkoxylates e.g. ethoxylates, particularly of $C_8$ to $C_{18}$ alkylamines; sorbitol and sorbitan fatty acid, particularly $C_8$ to $C_{18}$ fatty acid, esters and their ethoxylated derivatives; and alkyl, particularly $C_6$ to $C_{14}$ alkyl, polysaccharides. Solid adjuvants can be included directly in the formulation. When the adjuvant is a liquid then often simple direct incorporation is not appropriate because the adjuvant will often represent a relatively high proportion of the total weight of the granule. For example, typical weight ratios of adjuvant to agrochemical active range from 1:3 to 10:1. The inclusion of such a large amount of liquid may adversely affect the properties of the granule e.g. by making the granules sticky. This problem can be avoided by adsorbing the liquid adjuvant in or adsorbing it on a solid support e.g. silica or diatomaceous earth, which can be solid support, filler or diluent material as mentioned above, or by including it as a clathrate especially a urea clathrate.

Other surfactants can be included particularly as wetting agents to speed up granule wetting and disintegration on mixing with water. Examples of wetting agents include nonionic surfactants such as alcohol ethoxylates for example of $C_9$ to $C_{15}$, particularly primary, alcohols, which may be linear or branched, particularly mono-branched, ethoxylates with from 5 to 30 moles of ethylene oxide; and alkoxylates of such alcohols particularly mixed ethoxylate/propoxylates which may be block or random mixed alkoxylates, typically containing from 3 to 10 ethylene oxide residues and from 1 to 5 propylene oxide residues, particularly where the polyalkoxylate chain is terminated with propylene oxide unit(s); polyoxyethylene/polyoxypropylene copolymers, particularly block copolymers, such as the Synperonic PE series of copolymers and Atlas G 5000 available from Uniqema, and alkyl polysaccharides; anionic surfactants e.g. isethionates, such as sodium cocoyl isethionate, naphthalene sulphonic acids or sulphosuccinates. Mixtures of such wetting agents can also be used. Although some wetting agents are liquid, the amounts used are generally not so large as to give rise to problems with granule stickiness. However, if desired, the wetting agents can be used in a form in which they are adsorbed on solid support such as silica or diatomaceous earth, which can be solid support, filler or diluent material as mentioned above. Of course for solid wetting agents granule stickiness does not generally limit the amount that can be used even without using a support.

Water soluble matrix materials such as urea, ethylurea, hydroxyethylcellulose, sugars such as sorbitol and lactose, polyvinyl alcohol and sodium acetate trihydrate may be included if desired. Such matrix materials, especially urea can be used in the form of clathrates incorporating other system components such as adjuvants (see above).

The total amount of dispersing agent used in the granules of this invention is typically from 3 to 10%, particularly from 5 to 8%, by weight of the dry granule. The amount of polymeric dispersant used is desirably at least 1% and more usually 2 to 10%, particularly from 5 to 8% by weight of the total dry granule formulation. When a combination of polymeric dispersant and conventional dispersing agents is used the polymeric dispersant desirably represents at least 50%, more usually at least 75%, of the total dispersing agent by weight. When wetting agents are used the amount used is typically from 1 to 5%, particularly 2 to 4%, by weight of the dry granule and the weight ratio of dispersing agent to wetting agent is desirably from 2:1 to 4:1. Generally, the combined amount of dispersing agent and wetting agent is from 3 to 10%, more usually 5 to 8% by weight of the total dry granule formulation.

The total amount of agrochemically active material will typically be from 10 to 95%, more particularly 20 to 90% by weight of the dry granule. When the granule does not include an adjuvant, the amount of agrochemically active material will typically be from 40 to 95%, more particularly 50 to 90% by weight of the dry granule. When an adjuvant is included the amount of agrochemically active material will typically be from 10 to 70%, more particularly 20 to 50% by weight of the dry granule and the amount of adjuvant from 10 to 50%, particularly 20 to 40%, by weight of the total dry granule. Typically the amount of adjuvant is from 1 to 10, more usually from 1 to 5, parts by weight per part by weight of active. The combined proportion of agrochemically active material and adjuvant is typically from 10 to 95%, more particularly 20 to 90% by weight of the dry granule.

The amount of solid support, filler and/or diluent, when used, is typically from 0.05 to 2, particularly 0.1 to 1, parts by weight per part by weight of the combination of agrochemical active, adjuvant (when used), dispersing agent and wetting agent (when used). Thus, the amount of solid support material used is typically from 0 to 70%, particularly 5 to 50%, by weight of the dry granule. The amount of soluble diluent, when used, is typically from 0 to 70%, particularly 5 to 40%, by weight of the dry granule.

The amounts of the major components of the granules of the invention are desirably within the ranges indicated in the following table:

| Component | Amount (% w/w on dry granule) | | |
|---|---|---|---|
| | broad | preferred | |
| Agrochemical active | 10 to 95 | 20 to 90 | |
| without adjuvant | 40 to 95 | 50 to 90 | |
| with adjuvant | 10 to 70 | 20 to 50 | |
| Adjuvant (when present) | 10 to 50 | 20 to 40 | |
| Dispersing agent | 3 to 10 | 5 to 8 | |
| Polymeric dispersant | 1 to 10 | 5 to 8 | |
| Wetting agent (when present) | 1 to 5 | 2 to 4 | |
| combined Dispersing and Wetting agents | 3 to 10 | 5 to 8 | ratio dispersing to wetting agents particularly from 2:1 to 4:1 |
| Solid support (when present) | 0 to 70 | | |
| Soluble diluent (when present) | 0 to 70 | | |

Other materials that can be include in the granules include:

Buffering materials e.g. so that the pH of the redispersed material is from 4 to 9, more usually from 5 to 8 and particularly about 7.

Disintegrating agents can be included to speed granule disintegration on mixing with water e.g. in a spray mix tank. Suitable materials include readily soluble materials such as inorganic water soluble salts e.g. sodium chloride, nitrate salts etc., and water soluble organic compounds such as urea (water soluble matrix materials may thus serve also as disintegrating agents), which dissolve thus opening up the granule structure. More active disintegration effects can be achieved using materials which swell or are effervescent on contact with water. Such active disintegrants may be particularly useful where the granules are made by tabletting as tabletting tends to produce a more compacted solid form than other methods of granulation.

Humectants can be included, especially to aid water retention during granule formulation. Examples of suitable materials include polyoxyethylene/polyoxypropylene copolymers, particularly block copolymers, such as the Synperonic PE series of copolymers available from Uniqema. The non-ionic surfactants mentioned above as adjuvants may also act as humectants.

Particularly when the granules are made by tabletting, additional components may include lubricants such as stearates e.g. magnesium stearate, or boric acid, anti-adherence additives and glidants.

Other components that may be included are penetrating agents; antifoams; safeners such as Bitrex; pigments and/or dyes; anti-caking additives; sequestrants; and adhesives.

The solid granular form of the agrochemical formulations can be a powder, particularly to form a so-called wettable powder, which can be made by mixing the components in powdered form and passing the mixed powder through a centrifuge mill with a suitable e.g. a 0.08 mm, screen.

Typically, the granules are made by mixing the formulation components including sufficient water to form a paste having suitable rheology for granulation, forming granules from the mixture and then drying the granules. Desirably the formulation includes a filler and when used the composition of the formulation will usually be adjusted so that the composition can readily be formed into granules. A wide variety of granulation methods can be used, including extrusion, fluidized bed granulation, pan-granulation, spray drying and tabletting. Powder granular formulations can be converted into granules of larger particle size by such processing methods or by adding moderate amount of water to the powder and mixing to agglomerate the powder into larger granules.

In extrusion granulation the formulation will usually be made up as a pasty material that can readily extruded typically to give spaghetti like strands which are usually subsequently broken up into granules e.g. during drying.

In fluidized bed granulation a mixture of the powdered components is fluidized in a fluidized bed and the mixture is sprayed with an aqueous mixture or solution of the liquid components. The particles agglomerate in the bed to form granules which are dried in the bed.

In pan granulation, the solids are tumbled in a rotating inclined vessel and the liquid components sprayed on the particles which agglomerate to form granules which are dried either in the vessel or subsequently, e.g. in a fluidized bed drier.

In spray drying a flowable slurry or solution of all the components of the formulation is made and passed to a spray drier where the slurry or solution is atomised and dried. If necessary, a desired size range of particles is selected from the spray dried product and/or the product can be agglomerated e.g. in a fluidized bed, to form a granulate of the desired particle size range.

In making granules in the form of tablets the composition is made up in a form that is suitably plastic and is then tabletted.

Particularly where the granulation method directly produces granules having a range of particle sizes, the granule product can be sieved or otherwise classified, to yield a desired limited particle size range. This is a convenient way to exclude fine particles and thus to make a granular product which is non-dusting at the point of manufacture.

The granules of the agrochemical formulation of this invention typically can have a range of particle sizes. Granules having a moderate to large particle size, often described as water dispersible granules, can have an average particle size (based on spheres of equal volume) of from 200 $\mu$m to 1 cm more usually from 200 $\mu$m to 5 mm. As particle size and the rate of disintegration are usually inversely related, it is desirable that the particle size is not too great and average particle sizes of up to 2 mm, especially in the range 200 $\mu$m to 2 mm are used in water dispersible granule formulations for agrochemicals. An average particle size less that 200 $\mu$m is preferably not adopted as it will tend to be associated with higher proportions of fine particles that may give rise to dust. When the granules are made by extrusion, they typically have a diameter of from 0.5 to 2 mm but may retain a strand like form having a length of up to 1 cm, but more usually up to about 5 mm. Strand like granules of this type have minimum size, usually in two dimensions considerably less than their length and typically in the range 0.5 to 2 mm. When the granules are made by tabletting, the shape of the granules will primarily be set by the shape of the tablet mould and typical average granule sizes may be from 0.5 mm up to 7.5 mm more usually up to 5 mm. The other methods of making granules will typically yield particles having a low aspect ratio and will usually be made or selected to have an average particle size of from 200 $\mu$m to 2 mm, more usually 500 $\mu$m to 1.5 mm. As is indicated above, the particle size distribution will generally be chosen so that the presence of finer particles, particularly those less than about 100 $\mu$m is minimised. Accordingly the granules desirably include not more than about 2 weight %, desirably not more than 1 weight %, of particles having a size of less than 200 µm and desirably not more than 0.5% weight %, particularly not more than 0.1 weight %, of particles having a size of less than 50 µm.

Particularly where dusting is not a major issue, the granules can be in the form of a powder, as is commonly described as a wettable powder, and such powders typically have average particle sizes of from 2 to 100 µm, more usually 5 to 50 µm, and desirably 5 to 25 µm.

The following Examples illustrate the invention. All parts and percentages are by weight unless otherwise stated.

| Code | AA/Sty* | MW | |
|---|---|---|---|
| Dispersants - styrene acrylic acid copolymers: | | | |
| Materials | | | |
| DS1 | 2:1 | 3800 | ca 40% by weight active material in water |
| DS2 | 2:1 | 8000 | ca 40% by weight active material in water |
| DS3 | 5:1 | 4700 | ca 40% by weight active material in water |
| DS4 | 10:1 | 3800 | ca 40% by weight active material in water |
| DS5 | 10:1 | 7950 | ca 40% by weight active material in water |
| DS6 | 1:1 | 930 | ca 40% by weight active material in water |
| DS7 | 2:1 | 3800 | 90% by weight active material (DS1 spray dried) |
| DS8 | 2:1 | 8000 | 30% by weight active material in water |
| DS9 | 2:1 | 42000 | 20% by weight active material in water |
| DS10 | 2:1 | 1300 | acrylic monomer includes 10 mole % acrylamido methyl propyl sulphonate-40% by weight active material in water |

| Code | Commercial name | Description |
|---|---|---|
| Dispersants - other Dispersants | | |
| CDS1 | Morwet D425 | 88–90% by weight active, Na-salt of naphthalene sulphonic acid formaldehyde condensates broad MW distribution, methyl or isopropyl capped on naphthalene, ex Witco |
| CDS2 | Versa TL3 | sulphonated styrene maleic anhydride (SMA) Na salt ex National Starch Company |
| CDS3 | Versa TL130 | sulphonated polystyrene MW 200000 ex National Starch Company |
| CDS4 | Versa TL502 | sulphonated polystyrene MW 1000000 ex National Starch Company |
| CDS5 | Polyfon O | Sodium lignosulfonate ex Westvaco |
| Agrochemical Actives | | |
| Act1 | Atrazine | 99% by weight active material ex Novartis (Ciba) |
| Act2 | Diuron | 96 (min) % by weight active material in ex Sanachem |
| Act3 | Cu(OH)$_2$ | contains ca 60% by weight by weight Cu |
| Act4 | Chlorotalonil | 95 (min) % by weight active material ex Zeneca |
| Act5 | Iprodione | 95 (min) % by weight active material ex Rhone-Poulenc |
| Act6 | Tebuconazole | 95 (min) % by weight active material ex Bayer |
| Act7 | Carbaryl | 95 (min) % by weight active material ex Rhone-Poulenc |
| Other Materials | | |
| 342 water | | 342 ppm hardness WHO standard hard water |
| Surf1 | Atlox MBA 13/8 | alcohol ethoxylate surfactant ex Uniqema |
| Surf2 | Morwet EFW | Na-salt of naphthalene sulphonic acid formaldehyde ex Witco |
| Fill1 | Argirec B 24 | kaolin ex Blancs Minereaux de Paris |

*molar acrylic acid to styrene monomer ratio in copolymer

Test Methods

Suspensibility (%)

In Example 1 to 7, suspensibility—a measure for the stability of the dispersed solids in water—was assessed by dispersing 3 g of the granular formulation in 100 ml of 342 water in a test cylinder. The cylinder was inverted 30 times and allowed to stand for 30 minutes. The upper 90% were are drawn off with a suction tube, taking care not to disturb the sediment. The remaining liquid and any sediment were transferred to an evaporating dish and dried in an oven at 50° C. to constant weight. The resulting powder was weighed (y g). The suspensibility (%) is the concentration of the powder in the upper 90% of the water—expressed as:

$$[111.(3-y)/3]\% \text{ [equivalent to } 33.(3-y)\%/]$$

In Examples 8 and 9 suspensibility was measured by a modified method in which 1 g of the granular formulation was dispersed into 100 ml 342 ppm hardness water in a test cylinder, the cylinder was inverted 10 times and allowed to stand for 5 minutes, the cylinder again inverted 10 times and allowed to stand for 30 minutes. The upper 90% were drawn off with a suction tube, taking care not to disturb the sediment. The remaining material was filtered through a preweighed filter paper, dried and re-weighed to determine the weight of material unsuspended (y'g). The suspensibility (%) is the concentration of the powder in the upper 90% of the water—expressed as:

$$[111.(1-y)1] \%$$

Disintegration (%)

Disintegration—the ease with which the granules disintegrate in the aqueous dispersing medium—is measured by placing 4 g of granules in a test tube containing 100 ml of 342 water. The tube is inverted 10 times and the dispersion poured over a 150 µm sieve. The proportion of the granules retained on the sieve is measured (x %) and the Disintegration (%) is: (100-x)%

Ageing:

The effect of ageing on the granules was assessed by storing the granules at ambient temperature or in an oven at 50° C. The disintegration or suspensibility of the granules was assessed fresh (0) and reassessed after storage for periods of time from e.g. 1 week (1W), 10 days (10D), 1 month (1M) or 3 months (3M). The temperature of ageing is indicated as ambient (A) or 50° C. (50)

Manufacturing method

For test purposes granules were prepared in 100 g lots. The weight of agrochemical active, polymeric dispersant and wetting agent varied within the experimental design and solid support material was added in an amount that the total weight was 100 g. 342 water was added to the blend to form a homogenous paste with a satisfactory rheology profile for extrusion. This paste was fed to a Benchtop Granulator (Fuji Paudal) where it was passed through screens to give spaghetti like strands. These strands were dried in a fluid bed dryer (Niro Aromatic) at 40° C. for 20 minutes. The product broke down into granules by the mechanical action of the fluid bed drier and the granules were separated by sieving to give approximately cylindrical strands having an average (cylinder) diameter of from 1 to 1.5 mm which were up to about 5 mm long.

EXAMPLE 1

This Example illustrates the suspensibility of Atrazine formulations using various concentrations of different dispersing agent, including DS1 and various comparative materials. The basic formulation used was:

| | |
|---|---|
| Atrazine | 90 g |
| Atlox MBA 13/8 | 1.8 g |
| dispersing agent (dry) | 5.0 to 7.7 g (see Table 1) |
| Argirec B24 | to 100 g |

The suspensibility of the granules—fresh and aged—was tested and the results are set out in Table 1 below.

TABLE 1

| | dispersing agent | | suspensibility (%) | | | |
|---|---|---|---|---|---|---|
| Ex No | Nature | conc (wt %) | 0 | 1W50 | 1M50 | 3M50 |
| 1.1 | DS1 | 7.7 | 86 | 87 | 85 | NA |
| 1.2 | DS1 | 6 | 86 | 84 | 83 | 83 |
| 1.3 | DS1 | 5 | 86 | 84 | 84 | 84 |
| C1.1 | CDS1 | 7.7 | 89 | 78 | 69 | NA |
| C1.2 | CDS1 | 5 | 79 | 34 | 29 | NA |
| C1.3 | CDS2 | 7.7 | 89 | 91 | 86 | 89 |
| C1.4 | CDS2 | 6 | 87 | 82 | 82 | 78 |
| C1.5 | CDS2 | 5 | 78 | 78 | 57 | 58 |
| C1.6 | CDS3 | 7.7 | 90 | 90 | 86 | 85 |
| C1.7 | CDS3 | 6 | 86 | 86 | 84 | 54 |
| C.18 | CDS3 | 5 | 86 | 87 | 85 | 58 |
| C1.9 | CDS4 | 7.7 | 93 | 93 | 86 | 79 |
| C1.10 | CDS4 | 6 | 90 | 88 | 84 | 62 |
| C1.11 | CDS4 | 5 | 84 | 83 | 84 | 48 |

The superiority of DS1 over the comparative materials is clear especially at lower proportions of dispersing agent and after ageing.

EXAMPLE 2

In this Example various styrene acrylic acid copolymers were used as dispersing agents at 6% by weight (dry) (as in Example 1.2 above) and the effect on suspensibility of Atrazine was tested. The results are set out in Table 2 below.

TABLE 2

| | Dispersing | suspensibility (%) | |
|---|---|---|---|
| Ex No | agent | 0 | 1W50 |
| 2.1 | DS1 | 86 | 84 |
| 2.2 | DS2 | 81 | 75 |
| 2.3 | DS3 | 81 | 75 |
| 2.4 | DS4 | 83 | 72 |
| 2.5 | DS5 | 80 | 69 |
| 2.6 | DS6 | 83 | 75 |

EXAMPLE 3

Granules of 90% by weight atrazine and different concentrations of DS1, CDS2, CDS3 and CDS4 as dispersing-agent were made by extrusion of the mixture of the components. The disintegration of the fresh and aged granules was measured and the results are set out in Table 3 below.

TABLE 3

| | dispersing agent | | disintegration (%) | | |
|---|---|---|---|---|---|
| Ex No | type | conc (wt %) | 0 | 1M50 | 3M50 |
| 3.1 | DS1 | 7.7 | 95 | 95 | 95 |
| 3.2 | DS1 | 6 | 94 | 95 | 95 |
| 3.3 | DS1 | 5 | 95 | 95 | 95 |
| C3.1 | CDS2 | 7.7 | 95 | 95 | 86 |
| C3.2 | CDS2 | 6 | 95 | 76 | 87 |
| C3.3 | CDS2 | 5 | 95 | 68 | 90 |
| C3.4 | CDS3 | 7.7 | 83 | 91 | 76 |
| C3.5 | CDS3 | 6 | 86 | 63 | 98 |
| C3.6 | CDS3 | 5 | 86 | 68 | 97 |
| C3.7 | CDS4 | 7.7 | 81 | 82 | 58 |
| C3.8 | CDS4 | 6 | 58 | 63 | 90 |
| C3.9 | CDS4 | 5 | 59 | 52 | 86 |

EXAMPLE 4

In this Example the disintegration and suspensibility of water dispersible granules including 70% by weight Diuron as the active was tested. Granules were formulated with DS1 as dispersing agent and CDS1 for comparison, using the basic formulation:

| | |
|---|---|
| Diuron | 70 g |
| Atlox MBA 13/8 | 2 g |
| dispersing agent (dry) | 5 g (see table) |
| Argirec B24 | 23 g |

The test results are set out in table 4 below.

TABLE 4

| | dispersing | suspensibility (%) | | | disintegration (%) |
|---|---|---|---|---|---|
| Ex No | agent | 0 | 1W50 | 1M50 | 0 |
| 4.1 | DS1 | 70 | 70 | 60 | 95 |
| C4.1 | CDS1 | 70 | 70 | 50 | 95 |

EXAMPLE 5

This Example illustrates the use of $Cu(OH)_2$ as the active using the basic formulation:

| | |
|---|---|
| $Cu(OH)_2$ | 70 g |
| Atlox MBA 13/8 | 2 g |
| dispersing agent (dry) | 5 g (see table) |
| Argirec B24 | 23 g |

The suspensibility and dispersibility of the water dispersible granules were tested and the results set out in Table 5 below.

TABLE 5

| | dispersing | suspensibility (%) | | | disintegration (%) |
|---|---|---|---|---|---|
| Ex No | agent | 0 | 1W50 | 1M50 | 0 |
| 5.1 | DS1 | 67 | 51 | 47 | 80 |
| C5.1 | CDS1 | 45 | 46 | 41 | 90 |

EXAMPLE 6

Samples of wettable powder (WP) and water dispersible granules (WDG) of chlorotalonil were made in lots of about 200 g as follows:

proportional amounts of ingredients (see table 6a) were mixed until uniform in a glass jar;

the blended formulations were passed through a Centrifuge Mill at 18000 rpm (300 Hz), having a 0.08 mm screen;

5 to 10 g of the immediate product were set aside as samples of WP;

the remaining known weight of powder was added to a bread kneader and sufficient water to form a kneadable "dough" was added;

granules were extruded and were dried overnight at 50° C.

TABLE 6a

| | active | | dispersant | | wetter | | Filler | |
|---|---|---|---|---|---|---|---|---|
| Ex No | type | wt % | type | wt % | type | wt % | type | wt % |
| 6.1 | Act4 | 25 | DS7 | 7 | Surf2 | 1 | Fill1 | 67 |
| C6.1 | Act4 | 25 | CDS1 | 7 | Surf2 | 1 | Fill1 | 67 |
| 6.2 | Act4 | 25 | DS7 | 7 | Surf2 | 3 | Fill1 | 65 |
| C6.2 | Act4 | 25 | CDS1 | 7 | Surf2 | 3 | Fill1 | 65 |
| 6.3 | Act4 | 75 | DS7 | 2 | Surf2 | 1 | Fill1 | 22 |
| C6.3 | Act4 | 75 | CDS1 | 2 | Surf2 | 1 | Fill1 | 22 |
| 6.4 | Act4 | 75 | DS7 | 2 | Surf2 | 3 | Fill1 | 20 |
| C6.4 | Act4 | 75 | CDS1 | 2 | Surf2 | 3 | Fill1 | 20 |
| 6.5 | Act4 | 75 | DS7 | 7 | Surf2 | 1 | Fill1 | 17 |
| C6.5 | Act4 | 75 | CDS1 | 7 | Surf2 | 1 | Fill1 | 17 |
| 6.6 | Act4 | 75 | DS7 | 7 | Surf2 | 3 | Fill1 | 15 |
| C6.6 | Act4 | 75 | CDS1 | 7 | Surf2 | 3 | Fill1 | 15 |
| 6.7 | Act4 | 50 | DS7 | 4.5 | Surf2 | 2 | Fill1 | 43.5 |
| C6.7 | Act4 | 50 | CDS1 | 4.5 | Surf2 | 2 | Fill1 | 43.5 |

The suspensibility of these WP and WDG were measured in 342 ppm water and the results (means of tests on replicate samples 2× for 6.1 to 6.6 and C6.C to C6.6 and 4× for 6.7 and C6.7) are set out in Table 6b below. These results show that the acrylic acid styrene copolymer is an effective dispersant for both WP and WDG granular forms, being significantly superior to the conventional dispersant, and the suspensibility of the WDG did not deteriorate to a major extent on ageing testing.

TABLE 6b

| | Suspensibility | | | | |
|---|---|---|---|---|---|
| | WP | WDG | | | |
| Ex No | 0 | 0 | 1MA | 2MA | 1M50 | 2M50 |
| 6.1 | 78 | 80 | 79 | 82 | 80 | 79 |
| C6.1 | 79 | 69 | 69 | 70 | 65 | 67 |
| 6.2 | 78 | 79 | 78 | 79 | 78 | 78 |
| C6.2 | 81 | 59 | 64 | 67 | 58 | 63 |
| 6.3 | 75 | 78 | 77 | 77 | 77 | 77 |
| C6.3 | 70 | 65 | 65 | 65 | 63 | 65 |
| 6.4 | 73 | 75 | 76 | 75 | 76 | 75 |
| C6.4 | 71 | 68 | 68 | 66 | 66 | 67 |
| 6.5 | 70 | 76 | 75 | 75 | 75 | 74 |
| C6.5 | 70 | 71 | 69 | 69 | 69 | 70 |
| 6.6 | 74 | 78 | 79 | 78 | 79 | 77 |
| C6.6 | 66 | 65 | 64 | 64 | 64 | 64 |
| 6.7 | 75 | 78 | 78 | 78 | 78 | 86 |
| C6.7 | 78 | 73 | 74 | 74 | 72 | 73 |

EXAMPLE 7

Samples of wettable powder (WP) and water dispersible granules (WDG) were made as described in Example 6 but using various active materials. The composition of the WP and WDG and the Suspensibility test results on freshly prepared materials are set out in Table 7 below.

TABLE 7

| | Dispersant | | Active | | Wetter | | Filler | | Susp (%) | |
|---|---|---|---|---|---|---|---|---|---|---|
| Ex No | type | wt % | type | wt % | type | wt % | type | wt % | WP | WDG |
| C7.1 | CDS1 | 4.5 | Act4 | 50 | Surf2 | 2 | Fill1 | 43.5 | 75 | 72 |
| C7.2 | | | Act5 | 50 | | | | | 84 | 32 |
| C7.3 | | | Act6 | 50 | | | | | 67 | 27 |
| C7.4 | | | Act7 | 50 | | | | | 88 | 83 |
| C7.5 | CDS5 | 4.5 | Act4 | 50 | Surf2 | 2 | Fill1 | 43.5 | 65 | 70 |
| C7.6 | | | Act5 | 50 | | | | | 83 | 74 |
| C7.7 | | | Act6 | 50 | | | | | 70 | 76 |
| C7.8 | | | Act7 | 50 | | | | | 89 | 89 |
| 7.1 | DS7 | 4.5 | Act4 | 50 | Surf2 | 2 | Fill1 | 43.5 | 78 | 78 |
| 7.2 | | | Act5 | 50 | | | | | 87 | 88 |
| 7.3 | | | Act6 | 50 | | | | | 71 | 80 |
| 7.4 | | | Act7 | 50 | | | | | 88 | 90 |

EXAMPLE 8

Samples of wettable powder (WP) of carbaryl were made as described in Example 6 using blends of dispersants DS7 and DS10. Solutions of the dispersants were blended at ratios of 100:0, 75:25, 50:50, 25:75, and 0:100, based upon dispersant solids weights, and allowed to dry overnight at 50° C. The resultant crystals were ground using a pestle and mortar. These disperant blends were formulated using various levels of the dispersant blends and the suspensibility of the formulations was evaluated in 2000 ppm hardness water. The compositions and test results are set out in Table 8 below. The suspensibiiity results indicate that the dispersant including sulphonated monomer residues gives improved suspensibility as compared with DS1 alone in the very hard test water. Even modest proportions of DS10 can substantially enhance the suspensibility of formulations mainly using dispersant DS7.

TABLE 8

| | Dispersant | | | Active | | Wetter | | Filler | | Susp |
|---|---|---|---|---|---|---|---|---|---|---|
| Ex No | DS7 ratio | DS10 | wt % | type | wt % | type | wt % | type | wt % | (%) |
| 8.1a | 100 | 0 | 5 | Act7 | 75 | Surf2 | 1 | Fill1 | 19 | 24 |
| 8.1b | | | 6 | | | | | | 18 | 24 |
| 8.1c | | | 7 | | | | | | 17 | 23 |
| 8.2a | 75 | 25 | 5 | Act7 | 75 | Surf2 | 1 | Fill1 | 19 | 77 |
| 8.2b | | | 6 | | | | | | 18 | 81 |
| 8.2c | | | 7 | | | | | | 17 | 76 |
| 8.3a | 50 | 50 | 5 | Act7 | 75 | Surf2 | 1 | Fill1 | 19 | 88 |
| 8.3b | | | 6 | | | | | | 18 | 80 |
| 8.3c | | | 7 | | | | | | 17 | 89 |
| 8.4a | 75 | 25 | 5 | Act7 | 75 | Surf2 | 1 | Fill1 | 19 | 90 |
| 8.4b | | | 6 | | | | | | 18 | 90 |
| 8.4c | | | 7 | | | | | | 17 | 91 |
| 8.5a | 0 | 100 | 5 | Act7 | 75 | Surf2 | 1 | Fill1 | 19 | 85 |
| 8.5b | | | 6 | | | | | | 18 | 86 |
| 8.5c | | | 7 | | | | | | 17 | 93 |

EXAMPLE 9

Samples of water dispersible granules of carbaryl were made as described in Example 6 using blends of dispersants DS7 and DS10 as described in Example 8 at ratios of 75:25 and 50:50. These disperant blends were formulated using various levels of the dispersant blends and the suspensibility of the formulations was evaluated in 345 ppm and 2000 ppm hardness water initially and after 10 days storage at 50° C. Comparisons using conventional dispersants CDS1 and CDS5 were also made and tested. The compositions and test results are set out in Table 9 below. The results indicate that the dispersant including sulphonated monomer residues gives benefits in improved suspensibility in the very hard test water, particularly as compared with the conventional dispersants CDS1 and CDS5.

TABLE 9

| Ex | Dispersant | | | Active | | Wetter | | Filler | | Susp (%) | | |
|---|---|---|---|---|---|---|---|---|---|---|---|---|
| | | | | | | | | | | 0 | | 10D50 |
| No | type | ratio | wt % | type | wt % | type | wt % | type | wt % | 342 | 1000 | 1000 |
| 9.1a | DS7/ | 75  25 | 5 | Act7 | 75 | Surf2 | 1 | Fill1 | 19 | 95 | 85 | 85 |
| 9.1b | DS10 | | 6.5 | | | | | | 17.5 | 93 | 88 | 87 |
| 9.2a | DS7/ | 50  50 | 5 | Act7 | 75 | Surf2 | 1 | Fill1 | 19 | 93 | 192 | 91 |
| 9.2b | DS10 | | 6.5 | | | | | | 17.5 | 93 | 93 | 92 |
| C9.1a | CDS1 | | 5 | Act7 | 75 | Surf2 | 1 | Fill1 | 19 | 91 | 77 | 80 |
| C9.1b | | | 6.5 | | | | | | 17.5 | 91 | 78 | 81 |
| C9.2a | CDS5 | | 5 | Act7 | 75 | Surf2 | 1 | Fill1 | 19 | 94 | 37 | 41 |
| C9.2b | | | 6.5 | | | | | | 17.5 | 93 | 50 | 55 |

What is claimed is:

1. An agrochemical formulation in solid granular form which is dispersible in water and which comprises:
   1) one or more water dispersible agrochemical active components; and
   2) a dispersing agent comprising a water dispersible styrene (meth)acrylic copolymer; and
   wherein, the average particle size of the granules is from 200 μm to 1 cm.

2. An agrochemical formulation as claimed in claim 1 which further comprises at least one of:
   3) one or more solid support materials;
   4) one or more wetting agents;
   5) one or more adjuvants; and/or
   6) one or more water soluble matrix materials.

3. An agrochemical formulation as claimed in claim 1 which comprises:
   1) said one or more water dispersible agrochemical active components;
   2) a said dispersing agent comprising a water dispersible styrene (meth)acrylic copolymer;
   3) one or more solid support materials; and
   4) one or more wetting agents; and optionally
   5) one or more adjuvants; and/or
   6) one or more water soluble matrix materials.

4. An agrochemical formulation as claimed in claim 1 wherein in the styrene (meth)acrylic copolymer the (meth) acrylic acid monomer is acrylic acid, methacrylic acid, crotonic acid or a mixture of two or more of these and the styrene monomer is styrene or an alkyl substituted styrene.

5. An agrochemical formulation as claimed in claim 1 wherein the styrene (meth)acrylic copolymer includes (meth)acrylic acid monomer residues including a strong acid (or their salts).

6. An agrochemical formulation as claimed in claim 5 wherein the strong acid groups are sulphonic acid groups.

7. An agrochemical formulation as claimed in claim 1 wherein in the styrene (meth)acrylic copolymer the molar ratio of the residues of the (meth)acrylic acid monomer to those of the styrene monomer is from 10:1 to 1:2.

8. An agrochemical formulation as claimed in claim 1 wherein the styrene (meth)acrylic copolymer includes residues of one or more of itaconic acid, maleic acid or anhydride, acrylic alkyl esters, acrylic hydroxy alkyl esters, or vinyl.

9. An agricultural formulation as claimed in claim 8 wherein the styrene (meth)acrylic copolymer includes residues of one or more of methyl methacrylate, butyl (meth) acrylate, hydroxy ethyl methacrylate, or hydroxy propyl methacrylate.

10. An agrochemical formulation as claimed in claim 1 wherein the agrochemical Active Component comprises one or more of plant growth regulators, herbicides, or pesticides.

11. An agrochemical formulation as claimed in claim 1 in the form of a water dispersible granule having an average Particle size of from 200 μm to 5 mm.

12. A method of making a spray mix in which an agrochemical formulation in solid granular form as claimed in claim 1 is dispersed in water.

13. A method of treating plants in which the plants or the soil surrounding the plants are sprayed with a spray mix made by dispersing an agrochemical formulation in solid granular form as claimed in claim 1 in water.

14. An agrochemical formulation as claimed in claim 5 wherein the (meth)acrylic acid monomer residues including strong acid groups is acrylamido methyl propyl sulphonate or (meth)acrylic acid isethionate.

15. An agrochemical formulation as claimed claim 1 wherein in the styrene (meth)acrylic copolymer the molar ratio of the residues of the (meth)acrylic acid monomer to those of the styrene monomer is from 3:1 to 1:1.

16. An agrochemical formulation as claimed in claim 10 wherein the agrochemical Active Component comprises one or more insecticide, fungicide, acaricide, nematocide, miticide, rodenticide, bactericide, molluscicide or bird repellant.

17. An agrochemical formulation as claimed in claim 1 wherein the granule takes the form of an extruded strand having a diameter of from 0.5 to 2 mm and a length of up to 1 cm.

18. An agrochemical formulation in wettable powder form which is dispersible in water and which comprises:
   1) one or more water dispersible agrochemical active components; and
   2) a dispersing agent comprising a water dispersible styrene (meth)acrylic copolymer; and
   wherein the wettable powder has an average particle size of from 2 to 100 μm.

19. An agrochemical formulation as claimed in claim 18 which further comprises at least one of:
   3) one or more solid support materials;

4) one or more wetting agents;
5) one or more adjuvants; and/or
6) one or more water soluble matrix materials.

20. An agrochemical formulation as claimed in claim 18 which further comprises:
1) said one or more water dispersible agrochemical active components;
2) said dispersing agent comprising a water dispersible styrene (meth)acrylic copolymer;
3) one or more solid support materials; and
4) one or more wetting agents; and optionally
5) one or more adjuvants; and/or
6) one or more water soluble matrix materials.

21. An agrochemical formulation as claimed in claim 18 wherein the molar ratio of the residues of the (meth)acrylic acid monomer to those of the styrene monomer is from 10:1 to 1:2.

22. An agrochemical formulation as claimed in claim 18 wherein in the styrene (meth)acrylic copolymer the (meth)acrylic acid monomer is acrylic acid, methacrylic acid, crotonic acid or a mixture of two or more of these and the styrene monomer is styrene or an alkyl substituted styrene.

23. An agrochemical formulation as claimed in claim 18 wherein the styrene (meth)acrylic copolymer comprises (meth)acrylic acid monomer residues including a strong acid, (or their salts).

24. An agrochemical formulation as claimed in claim 23 wherein the strong acid groups are sulphonic acid groups.

25. An agrochemical formulation as claimed in claim 24 wherein the (meth)acrylic acid monomer residues including strong acid groups is acrylamido methyl propyl sulphonate or (meth)acrylic acid isethionate.

26. An agrochemical formulation as claimed in claim 18 wherein in the styrene (meth)acrylic copolymer the molar ratio of the residues of the (meth)acrylic acid monomer to those of the styrene monomer is from 3:1 to 1:1.

27. An agrochemical formulation as claimed in claim 18 wherein the styrene (meth)acrylic copolymer includes residues of one or more of itaconic acid, maleic acid or anhydride, acrylic alkyl esters, acrylic hydroxy alkyl esters, or vinyl acetate.

28. An agrochemical formulation as claimed in claim 18 wherein the styrene (meth)acrylic copolymer includes residues of one or more of methyl methacrylate, butyl (meth)acrylate, hydroxy ethyl methacrylate, or hydroxy propyl methacrylate.

29. An agrochemical formulation as claimed in claim 18 wherein the agrochemical Active Component comprises one or more plant growth regulators, herbicides, and/or pesticides.

30. An agrochemical formulation as claimed in claim 29 wherein the agrochemical Active Component comprises one or more insecticide, fungicide, acaricide, nematocide, miticide, rodenticide, bactericide, molluscicide or bird repellent.

31. An agrochemical formulation as claimed in claim 18 the form of a wettable powder having an average particle size of from 5 to 50 μm.

32. A method of making a spray mix in which an agrochemical formulation as claimed in claim 18 is dispersed in water.

33. A method of treating plants in which the plants or the soil surrounding the plants are sprayed with a spray mix made by dispersing an agrochemical formulation as claimed in claim 18 in water.

34. An agrochemical formulation in solid granular form which is dispersible in water and which includes:
1) one or more water dispersible agrochemical active components; and
2) a first dispersing agent comprising a water dispersible styrene (meth)acrylic copolymer including residues of a (meth)acrylic monomer which includes strong acid groups.

35. An agrochemical formulation as claimed in claim 34 which further comprises at least one of:
3) one or more solid support materials;
4) one or more wetting agents;
5) one or more adjuvants; and/or
6) one or more water soluble matrix materials.

36. An agrochemical formulation as claimed in claim 34 which comprises:
1) said one or more water dispersible agrochemical active components;
2) said first dispersing agent;
3) one or more solid support materials; and
4) one or more wetting agents; and optionally
5) one or more adjuvants; and/or
6) one or more water soluble matrix materials.

37. An agrochemical formulation as claimed in claim 34 wherein in the styrene (meth)acrylic copolymer the (meth)acrylic acid monomer is acrylic acid, methacrylic acid, crotonic acid or a mixture of two or more of these and the styrene monomer is styrene or an alkyl substituted styrene.

38. An agrochemical formulation as claimed in claim 34 wherein the strong acid groups are sulphonic acid groups (or their salts).

39. An agrochemical formulation as claimed in claim 38 wherein the (meth)acrylic acid monomer residues including strong acid groups is acrylamido methyl propyl sulphonate or (meth)acrylic acid isethionate.

40. An agrochemical formulation as claimed in claim 38 wherein the proportion of (meth)acrylic acid monomer residues including strong acid groups is from 2 to 20 mole %.

41. An agrochemical formulation as claimed in claim 40 wherein the overall proportion of monomer residues including strong acid groups is from 5 to 15 mole %.

42. An agrochemical formulation as claimed in claim 34 wherein in the styrene (meth)acrylic copolymer the molar ratio of the residues of the (meth)acrylic acid monomer to those of the styrene monomer is from 10:1 to 1:2.

43. An agrochemical formulation as claimed claim 34 wherein in the styrene (meth)acrylic copolymer the molar ratio of the residues of the (meth)acrylic acid monomer to those of the styrene monomer is from 3:1 to 1:1.

44. An agrochemical formulation as claimed in claim 34 wherein the styrene (meth)acrylic copolymer includes residues of one or more of itaconic acid, maleic acid or anhydride, acrylic alkyl esters, acrylic hydroxy alkyl esters, or vinyl acetate.

45. An agrochemical formulation as claimed in claim 34 wherein the styrene (meth)acrylic copolymer includes residues of one or more of methyl methacrylate, butyl (meth)acrylate, hydroxy ethyl methacrylate, or hydroxy propyl methacrylate.

46. An agrochemical formulation as claimed in claim 34 further comprising at least one second dispersant copolymer comprising a water dispersible styrene (meth)acrylic copolymer in which the molar ratio of the residues of the (meth)acrylic acid monomer to those of the styrene monomer is from 10:1 to 1:2.

47. An agrochemical formulation as claimed in claim 34 wherein the copolymer including strong acid residues comprises at least 25%, by weight of the first and second dispersants.

48. An agrochemical formulation as claimed in claim 34 wherein the agrochemical active comprises one or more plant growth regulators, herbicides, and/or pesticides.

49. An agrochemical formulation as claimed in claim 48 wherein the agrochemical Active Component comprises one or more of insecticides, fungicides, acaricides, nematocides, miticides, rodenticides, bactericides, molluscicides and bird repellants.

50. An agrochemical formulation as claimed in claim 34 the form of a wettable powder having an average particle size of from 2 to 100 $\mu$m.

51. An agrochemical formulation as claimed in claim 34 in the form of a water dispersible granule having an average particle size of from 200 $\mu$m to 5 mm.

52. A method of making a spray mix in which an agrochemical formulation in solid granular form as claimed in claim 34 is dispersed in water.

53. A method of treating plants in which the plants or the soil surrounding the plants are sprayed with a spray mix made by dispersing an agrochemical formulations in solid granular form as claimed in claim 34 in water.

54. A spray mix made by the method of claim 12.

55. A spray mix made by the method of claim 32.

56. A spray mix made by the method of claim 52.

* * * * *